US009259165B2

(12) United States Patent
Rubinstein et al.

(10) Patent No.: US 9,259,165 B2
(45) Date of Patent: Feb. 16, 2016

(54) DETERMINATION OF REFERENCE ANNOTATION TIME FROM MULTI-CHANNEL ELECTRO-CARDIOGRAM SIGNALS

(71) Applicant: BIOSENSE WEBSTER (ISRAEL) LTD., Yokneam (IL)

(72) Inventors: Vladimir Rubinstein, Haifa (IL); Meir Bar-Tal, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 14/190,176

(22) Filed: Feb. 26, 2014

(65) Prior Publication Data

US 2015/0238102 A1   Aug. 27, 2015

(51) Int. Cl.
| A61B 5/0402 | (2006.01) |
| A61B 5/04 | (2006.01) |
| A61B 5/0408 | (2006.01) |
| A61B 5/00 | (2006.01) |
| A61B 5/042 | (2006.01) |
| A61B 5/0456 | (2006.01) |

(52) U.S. Cl.
CPC ........... *A61B 5/04014* (2013.01); *A61B 5/0402* (2013.01); *A61B 5/0408* (2013.01); *A61B 5/04012* (2013.01); *A61B 5/0422* (2013.01); *A61B 5/04028* (2013.01); *A61B 5/0456* (2013.01); *A61B 5/04085* (2013.01); *A61B 5/7203* (2013.01); *A61B 5/7221* (2013.01); *A61B 5/7275* (2013.01); *A61B 5/7235* (2013.01); *A61B 5/7282* (2013.01)

(58) Field of Classification Search
None
See application file for complete search history.

(56) References Cited

U.S. PATENT DOCUMENTS

| 5,391,199 | A | * | 2/1995 | Ben-Haim ..................... 607/122 |
| 6,206,874 | B1 | * | 3/2001 | Ubby et al. ..................... 606/34 |
| 7,949,390 | B1 | | 5/2011 | Wirasinghe et al. |
| 2002/0010392 | A1 | * | 1/2002 | Desai ............................ 600/374 |
| 2002/0065459 | A1 | | 5/2002 | MacAdam et al. |
| 2009/0076403 | A1 | | 3/2009 | Hopenfeld |
| 2009/0099468 | A1 | | 4/2009 | Thiagalingam et al. |
| 2012/0184858 | A1 | | 7/2012 | Harlev et al. |
| 2013/0123652 | A1 | | 5/2013 | Rubinstein |

FOREIGN PATENT DOCUMENTS

| EP | 1872715 A1 | 1/2008 |
| WO | WO 2006/066324 A1 | 6/2006 |

OTHER PUBLICATIONS

U.S. Appl. No. 13/726,719, filed Dec. 26, 2012.
European Search Report received Jul. 1, 2015 for Application No. EP15156549.

* cited by examiner

*Primary Examiner* — Kennedy Schaetzle
(74) *Attorney, Agent, or Firm* — Louis J. Capezzuto

(57) ABSTRACT

A method includes receiving a plurality of mapping electro-cardiogram (ECG) signals from respective mapping electrodes coupled to a surface of a heart of a patient. Multiple reference ECG signals are received from respective reference electrodes coupled to the patient. The multiple reference ECG signals are jointly processed, so as to produce a single timing reference indicative of cardiac cycle timing of the heart. The single timing reference is applied to the mapping ECG signals.

18 Claims, 7 Drawing Sheets

US 9,259,165 B2

DETERMINATION OF REFERENCE ANNOTATION TIME FROM MULTI-CHANNEL ELECTRO-CARDIOGRAM SIGNALS

FIELD OF THE INVENTION

The present invention relates generally to signal analysis, and specifically to analysis of signals generated during a medical procedure.

BACKGROUND OF THE INVENTION

Electrophysiological (EP) cardiac mapping is a diagnostic medical procedure for identifying locations of cardiac dysfunction within a heart. Time-varying electro-cardiogram (ECG) signals are received by electrodes contacting points along the surface of a patient's heart. The signals are processed and different metrics regarding cardiac functions are computed from the processed (ECG) signals, which are then spatially mapped onto an image of the heart. The map is then outputted for a medical professional to analyze.

The analysis of cardiac signals sometimes involves synchronizing to the timing of the ECG signals. For example, U.S. Patent Application Publication 2013/0123652, whose disclosure is incorporated herein by reference, describes a method for analyzing signals, including sensing a time-varying intra-cardiac potential signal and finding a fit of the time-varying intra-cardiac potential signal to a predefined oscillating waveform. The method further includes estimating an annotation time of the signal responsive to the fit.

SUMMARY OF THE INVENTION

An embodiment of the present invention provides a method including receiving a plurality of mapping electro-cardiogram (ECG) signals from respective mapping electrodes coupled to a surface of a heart of a patient. Multiple reference ECG signals are received from respective reference electrodes coupled to the patient. The multiple reference ECG signals are jointly processed, so as to produce a single timing reference indicative of cardiac cycle timing of the heart. The single timing reference is applied to the mapping ECG signals.

In some embodiments, jointly processing the reference ECG signals includes selecting from among the reference ECG signals two or more preferable ECG signals that meet a signal quality criterion, and deriving the single timing reference from the selected preferable ECG signals.

In some embodiments, processing the ECG reference signals includes combining two or more of the reference ECG signals to produce an equivalent ECG function, and deriving the single timing reference from the equivalent ECG function. In other embodiments, deriving the single timing reference includes applying an adaptive threshold to the equivalent ECG function. In yet other embodiments, deriving the single timing reference includes computing a first moment of the equivalent ECG function.

In some embodiments, processing the ECG reference signals includes computing two or more timing references for two or more of the reference ECG signals, respectively, and deriving the single timing reference from the two or more timing references. In other embodiments, deriving the single timing reference includes averaging the two or more timing references. In yet other embodiments, averaging the two or more timing references includes calculating a weighted average of the two or more timing references depending on respective maximum amplitudes of the respective reference ECG signals.

In some embodiments, jointly processing the reference ECG signals includes detecting a missing peak in one of the reference ECG signals, and compensating for the missing peak in computation of the single timing reference. In other embodiments, jointly processing the reference ECG signals includes distinguishing between atrial and ventricular ECG signatures in the reference ECG signals.

There is also provided, in accordance with an embodiment of the present invention, an apparatus including an interface and a processor. The interface is configured to receive a plurality of mapping electro-cardiogram (ECG) signals from respective mapping electrodes coupled to a surface of a heart of a patient, and to receive multiple reference ECG signals from respective reference electrodes coupled to the patient. The processor is configured to jointly process the multiple reference ECG signals, so as to produce a single timing reference indicative of cardiac cycle timing of the heart, and to apply the single timing reference to the mapping ECG signals.

The present invention will be more fully understood from the following detailed description of the embodiments thereof, taken together with the drawings in which:

DETAILED DESCRIPTION OF EMBODIMENTS

Overview

Figure 1:
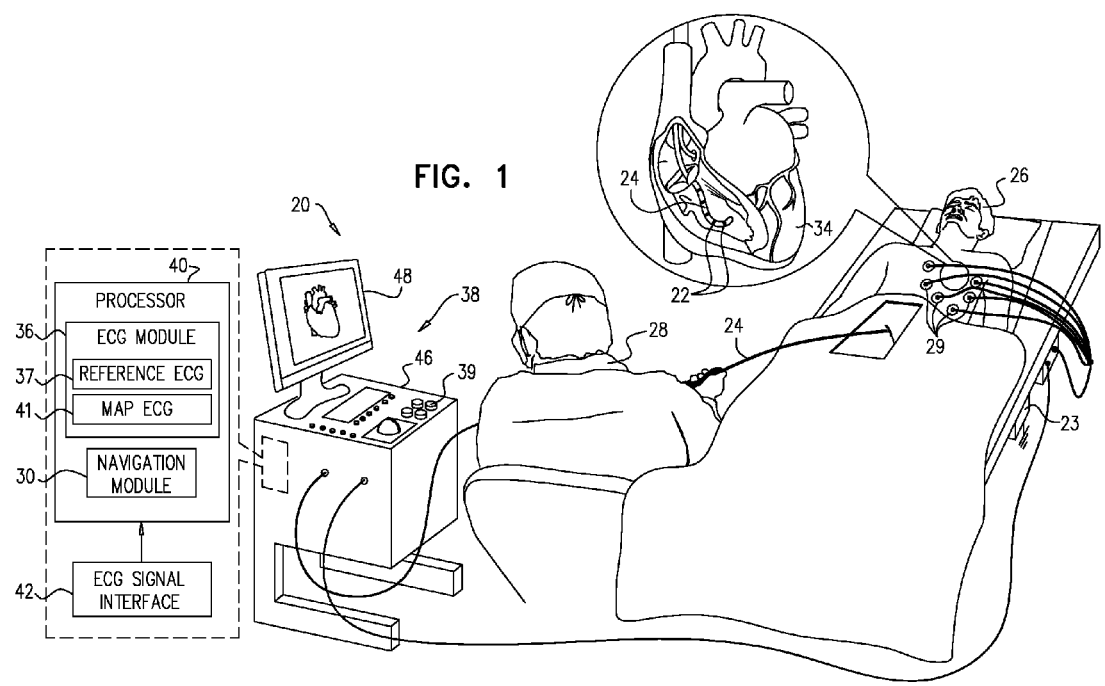
FIG. 1 is a schematic illustration of an electrocardiogram (ECG) analysis system 20, according to an embodiment of the present invention.

Electrophysiological (EP) cardiac mapping, or cardiac electro-anatomical mapping, is used to identify regions in the heart tissue that are dysfunctional. An intra-body probe, typically a catheter with multiple mapping electrodes disposed along the body of the catheter near the catheter distal end, is inserted into a cavity of the heart. Time varying electro-cardiogram (ECG) signals are recorded at multiple contact points between the mapping electrodes and the heart tissue. The multiple ECG electrodes are then moved to different contact positions with the heart tissue and the process is repeated. Then, metrics regarding cardiac function are computed from the local ECG signals, which are mapped spatially across the surface of the heart cavity. The mapping assists the medical professional to identify regions of heart dysfunction.

Electrical sources in the heart, such as the sinoatrial (SA) and atrioventricular (AV) nodes initiate electrical activity waves that propagate over the heart triggering the muscle tissue in the atria and ventricles to contract in a characteristic sinus rhythm. When the activity wave-front reaches the multiple mapping electrodes during each cardiac cycle, the characteristic ECG waveforms are detected at the multiple mapping electrodes. These waveforms are time-shifted due to the different arrival times of the same wave-front at the different multiple electrodes contacting the tissue at different spatial locations along the surface of the heart cavity.

The arrival times of the ECG waveforms detected at the multiple mapping electrodes can be used to map the propagation time and/or velocity of the activity wave across the heart. The mapping of the activity wave is performed with respect to a single time reference indicative of the cardiac cycle known herein as the reference annotation time.

The reference annotation time can computed by processing the ECG signals obtained from a body surface (BS) electrode, or from an intra-cardiac (IC) reference electrode on an additional catheter and placed in contact with the surface of the cardiac chamber. Typically, the physician designates whether the reference annotation time is computed from a BS or IC channel, depending on the suspected pathology. However, if during the course of the mapping procedure the assigned ECG reference channel fails (e.g., due to poor reference electrode contact, system noise, or other impairments), remapping needs to be performed. Remapping of the heart is time consuming and uncomfortable for the patient.

Embodiments of the present invention provide improved methods and systems for estimating the reference annotation time. In the disclosed embodiments, an ECG analysis system combines the outputs of multiple ECG channels to compute the reference annotation time. Some embodiments teach methods for computing the reference annotation time from multiple reference ECG signals acquired from body surface electrodes. Other embodiments describe methods for computing the reference annotation time from multiple reference ECG signals acquired from intra-cardiac ECG electrodes contacting multiple fixed points on the heart tissue, typically in the coronary sinus. The disclosed techniques combine multiple ECG signals to generate the reference annotation time, rather than relying on a single electrode. As such, the disclosed techniques are highly robust, stable and accurate.

Methods for handling impairments in the IC reference signals used for computing the reference annotation time are also taught. An example method compensates for missing ECG signals received from IC reference electrodes in adjacent cardiac cycles, for example resulting from poor electrode contact quality with the moving endocardium during heart beats. Other methods distinguish signatures of both atrial and ventricular ECG signals, which appear in the reference ECG signals.

System Description

FIG. 1 is a schematic illustration of an electrocardiogram (ECG) analysis system 20, according to an embodiment of the present invention. A probe 24 is percutaneously inserted into the body of a subject 26 during a cardiac mapping procedure performed by a user 28 of system 20. In the description herein user 28 is assumed, by way of example, to be a physician or other medical professional. In some embodiments, body surface electrodes 29 may be attached to the skin of subject 26, in the region of a heart 34. During the procedure subject 26 is assumed to be attached to a grounding electrode 23.

Probe 24 typically comprises a catheter. In the exemplary embodiment shown in FIG. 1, catheter 24 is navigated into the right ventricle of heart 34 as shown in the inset of FIG. 1. Multiple electrodes 22 are disposed along the length of catheter 24 for contacting the heart tissue.

For simplicity and clarity, the following description, except where otherwise stated, assumes a medical procedure that senses electrical signals from heart 34, using electrodes 22 disposed on catheter 24. Those ordinarily skilled in the art will be able to adapt the description for multiple probes having a plurality of electrodes, as well as for signals produced by organs other than a heart. Stated differently, any suitable number of catheters with respective electrode configurations may be navigated into the heart to perform the functions described herein.

When electrodes 22 contact the heart tissue, system 20 receives multiple electrical signals from the electrodes. For example, catheter 24 with a plurality of reference electrodes may be positioned in a reference region of the heart, such as in the coronary sinus, and used to sense reference ECG signals from the region.

System 20 may be controlled by a processor 40. Processor 40 is typically mounted in a console 46, which comprises operating controls 38. Controls 38 typically include a pointing device 39, such as a mouse or a trackball, that professional 28 uses to interact with the processor. The processor uses software, such as a probe navigation module 30 and an ECG module 36, to operate system 20. ECG module 36 further comprises a reference ECG sub-module 37 and a map ECG sub-module 41, whose functions are described below.

Results of the operations performed by processor 40 are presented to user 28 on a display 48, which typically presents a graphic user interface to the operator, a visual representation of the ECG signals sensed by electrodes 22 such as the cardiac map to be described later, and/or an image of heart 34 while it is being investigated. The software may be downloaded to processor 40 in electronic form, over a network, for example, or it may, alternatively or additionally, be provided and/or stored on non-transitory tangible media, such as magnetic, optical, or electronic memory.

System 20 also comprises an ECG signal interface 42 which is configured for receiving the ECG signals from electrodes 22 on catheter 24 and relaying the signals to processor 40. ECG module 36 is configured to analyze the received ECG signals and may present the results of the analysis in a standard ECG format, typically a graphical representation moving with time, on display 48.

Probe navigation module 30 tracks sections of probe 24 while the probe is within subject 26. The navigation module typically tracks both the location and orientation of the distal end of catheter 24, within the heart of subject 26. In some embodiments module 30 tracks other sections of the probe.

Navigation module 30 may use any method for tracking probes known in the art. For example, module 30 may operate magnetic field generators in the vicinity of the subject, so that magnetic fields from the field generators interact with tracking coils located in sections of the probe being tracked. The coils interacting with the magnetic fields generate signals which are transmitted to module 30, which analyzes the signals to determine a location and orientation of the coils. (For simplicity such coils and field generators are not shown in FIG. 1.) The Carto® system produced by Biosense Webster, of Diamond Bar, Calif., uses such a tracking method.

Alternatively or additionally, navigation module 30 may track probe 24 by measuring impedances between electrode 23, electrodes 29 and electrodes 22, as well as the impedances to other electrodes which may be located on the probe. (In this case electrodes 22 and/or electrodes 29 may provide both ECG and tracking signals as will be described later.) The Carto3® system produced by Biosense Webster uses both magnetic field generators and impedance measurements for tracking.

Figure 2:
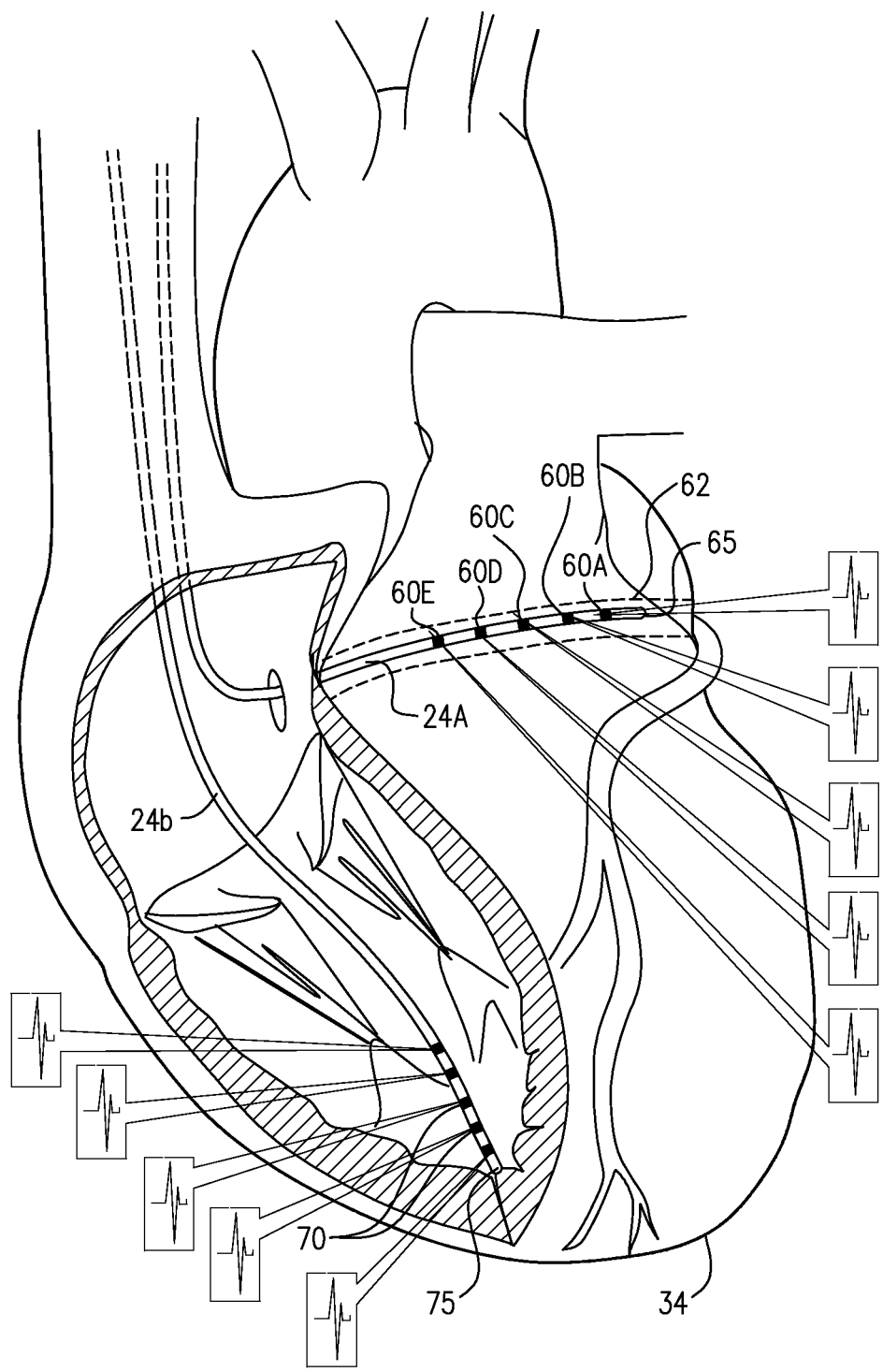
FIG. 2 is an illustration of a plurality of electrodes sampling multiple contact points in a heart cavity, in accordance with an embodiment of the present invention.

FIG. 2 is an illustration of a plurality of electrodes sampling multiple contact points in a heart cavity, in accordance with an embodiment of the present invention. In the exemplary embodiment shown in FIG. 2, intra-cardiac (IC) catheter 24A is inserted into a coronary sinus 62 of heart 34. The catheter comprises five reference ECG electrodes 60A . . . 60E disposed at points along the length of the body of catheter 24A near a distal end 65. Reference ECG electrodes 60A . . . 60E contact multiple tissue points on the surface of the coronary sinus and are used to measure respective reference ECG signals at the multiple contact points.

Similarly, IC catheter 24B is inserted into the right ventricle of heart 34. The catheter comprises five mapping electrodes 70 at points along the body of catheter 24B near a distal end 75. Mapping electrodes 70 contact multiple tissue points on the surface of the right ventricle and are used to measure respective mapping ECG signals at the multiple contact points.

ECG Signal interface 42 receives the signals from the body surface electrodes 29, IC ECG reference electrodes 60A . . . 60E and mapping electrodes 70. These signals are processed in ECG module 36 of processor 40. Reference ECG sub-module 37 processes signals from the reference ECG electrodes, and MAP ECG sub-module 41 processes signals from mapping electrodes 70.

The five reference ECG electrodes 60A . . . 60E and multiple mapping electrodes 70 shown in FIG. 2 are depicted merely for conceptual clarity and not by way of limitation of the present invention. In alternative embodiments, any suitable number of mapping and reference electrode configurations can be used. For example, instead of a single electrode for unipolar ECG detection, the electrodes can be arranged in pairs for bipolar ECG detection as described in the reference cited above. Any suitable number of mapping and reference catheters can be used in any suitable configuration such as in a spiral lasso catheter. Reference catheter 24A and mapping catheter 24B, or any number of catheters, could be navigated into a suitable location within heart 34 to perform the functions described herein.

Electro-Anatomical Mapping of the Cardiac Activation Wave

The normal sinus rhythm of the heart beats is initiated when the sinoatrial (SA) node in the heart initiates a depolarization wave over the atrial tissue resulting in atrial heart muscle contraction, pushing blood in the atria into the ventricles. Similarly, after a delay of about 70 ms, a depolarization wave initiating in the atrioventricular (AV) node passes over the ventricular heart tissue resulting in a ventricular muscle contraction pushing blood out of the ventricles. Repolarization waves "reset" the heart muscle tissue in both the atria and ventricles in preparation for the next heart beat. This electrical activity results in the classic ECG waveform morphology (e.g., P-wave, QRS-complex, T-wave) when detected, using ECG body electrodes 29.

The atrial and ventricular activation waves produced by the SA node and passes through AV node spread out over the heart muscle as a wave front with a spatially dependent propagation time. Mapping of the wave propagation time along with the voltage of the activation wave at points along the heart tissue may be used to detect local heart tissue dysfunction.

Cardiac mapping is performed by moving multiple electrodes 70 across the surface of the endocardial tissue and recording the ECG at each contact point along with the location of the electrode when the ECG waveform was recorded. Alternatively, cardiac mapping may comprise inserting reference and/or mapping electrodes externally into the patient's body, for example through the chest cavity, to contact the surface of the epicardial tissue. The term "surface" may thus refer to the endocardium or the epicardium.

The data recorded at each mapping point is also referred to herein as the mapping annotation. However, since the activation wave front propagates to the different electrodes at spatially different points on the endocardium, the local ECG signals arrive at different points, and thus to different electrodes, at different times.

The difference in the arrival time of the ECG signal to a given ECG electrode is an indication of the local activation wave front velocity. The difference between the measured time of the ECG signal arriving at a particular mapping electrode for a particular cardiac cycle, or heart beat, relative to a single timing reference indicative of cardiac cycle timing of the heart is known herein as the local activation time (LAT). Similarly, the single timing reference is known herein as the reference annotation time, the timing reference for system 20.

A typical cardiac map comprises a mapping of the LATs on multiple different points on the heart surface, a propagation map showing the activation wave front at different times across the heart, and characteristic voltages of the ECG at the same given points. User 28 can then use changes from the expected activity wave front and/or voltages shown in the cardiac map to detect regions of heart dysfunction, such as atrial or ventricular tachycardia. Ablation therapy, for example, may be used to correct the dysfunction.

In some embodiments, processor 40 uses acquired reference ECG signals in computing the reference annotation time from BS electrodes 29 and/or from IC reference electrodes 60A . . . 60E. Acquired IC mapping ECG signals are acquired as the mapping electrodes are moved across the endocardium and the ECG recorded for acquiring the mapping data points. However, the multiple IC reference electrodes contact the endocardium and are not moved during the medical procedure. Depending on the type of anticipated pathology, user 28 typically designates whether the reference annotation time is be computed from ECG taken from BS electrodes 29 or from IC reference electrodes 60A . . . 60E.

The reference annotation time may be acquired by identifying a particular position on the morphology of the ECG signal, such as for example, the R-wave peak, or by fitting techniques described in U.S. Patent Application Publication 2013/0123652 above for acquired a reference annotation time derived from a single ECG waveform channel.

The accuracy of the cardiac electro-anatomical mapping (e.g., LAT accuracy) is dependent on the stability of the reference annotation time. As the heart beats and the cardiac tissue moves, the contact between the endocardium and the IC reference electrode chosen from among electrode 60A . . . 60E may degrade. Noise may appear in the reference ECG channel, or any other impairment may suddenly appear impeding real time updates of the reference ECG signals during each heart beat used for the reference annotation time, (e.g., system 20 timing reference). If the reference ECG channel is lost, previous acquired mapping data may be lost and a new remapping procedure is needed.

Determination of the Reference Annotation Time from Multiple ECG Reference Channels In the embodiments of the present invention, processor 40 determines the reference annotation time jointly from multiple ECG reference channels during each cardiac cycle. Typically, IC electrodes 60A . . . 60E on catheter 24A and BS electrodes 29 are always detecting multiple signals. In the methods taught herein, multiple BS ECG reference signals, and/or multiple IC reference signals, are simultaneously used to determine the reference annotation time. Thus, if one of the ECG reference channels is impaired as described previously, the reference annotation time can still be determined without initiating a remapping procedure of system 20. The computed, or estimated, reference annotation time in each heart beat is then applied to the mapping annotations to compute the LAT maps as described below in the following flowcharts.

Figure 3:
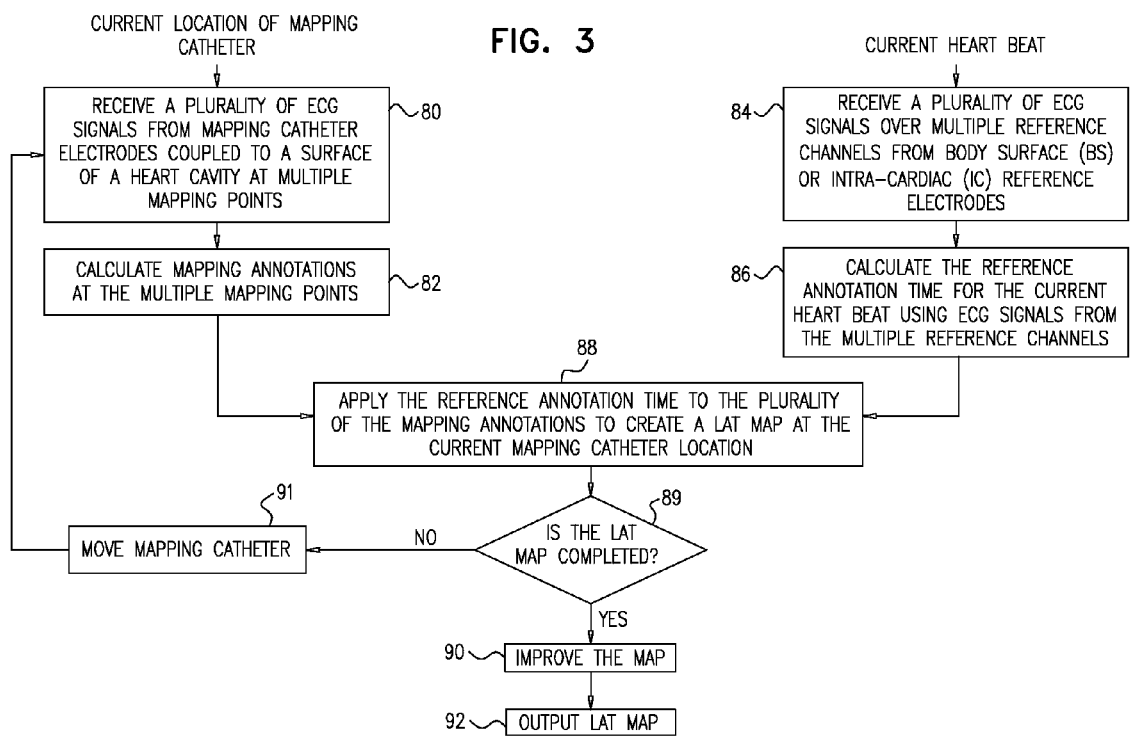
FIG. 3 is a flow chart that schematically illustrates a method for producing a local activation time map in a heart cavity, in accordance with an embodiment of the present invention.

FIG. 3 is a flow chart that schematically illustrates a method for creating a local activation time map in a heart cavity, in accordance with an embodiment of the present invention. Mapping catheter 24B is navigated to a location in the heart cavity. In a first receiving step 80, ECG signal interface 42 receives a plurality of electro-cardiogram (ECG) signals from mapping catheter electrodes 70 coupled to a surface of the heart cavity at multiple contact points. The term "surface" may refer to the endocardium or the epicardium as mentioned previously. In a first calculating step 82, map ECG sub-module 41 calculates mapping annotations at the multiple mapping points.

In a second receiving step 84, ECG signal interface 42 receives a plurality of ECG signals over multiple reference channels from body surface (BS) or intra-cardiac (IC) reference electrodes (e.g., from BS electrodes 29 or IC electrodes 60A . . . 60E, respectively) for the current heart beat. In a second calculating step 86, reference ECG module 37 calculates the reference annotation time for the current heart beat using ECG signals in the multiple reference channels.

In an applying step 88, processor 40 applies the reference annotation time to the plurality of the mapping annotations to create a LAT map at the current mapping catheter position. In a decision step 89, processor 40 assesses if the LAT map is completed. If not, in a moving step 91, mapping catheter 24B is moved to a new location in the heart cavity and the mapping process continues in receiving step 80.

If the LAT map is complete in decision step 89, the LAT map is improved in an improving step 90. The LAT mapping data is smoothed in relation to the position along the heart wall where the mapping electrodes acquired the data. This smoothing adjusts the LATs in the LAT map dataset before metrics such as the isochronal lines are computed. Example methods for improving the LAT map are described in U.S. patent application Ser. No. 13/726,719, filed Dec. 26, 2012, whose disclosure is incorporated herein by reference. Finally, in an outputting step 92, the LAT map is outputted to user 28.

Computing the reference annotation time from the multiple channels in calculating step 86 is typically dependent on the type of ECG reference electrode used, BS or IC, and is described as follows. First, ECG channels with robust, or "good" ECG signals are identified. An activity index (AI) function combines the ECG data from the multiple "good" channels into one equivalent ECG function, which is computed from the time-varying waveforms of the "good" ECG signals. From the activity index, a time segment is determined as an indicator where heart activity in the cardiac cycle occurs, known herein as the activity segment time, or the activity segment, typically the width of the activity index pulse. The reference annotation time is located with the activity segment and is computed by a number of methods to be described herein based on the whether BS or IC reference electrodes are used.

Figure 4:
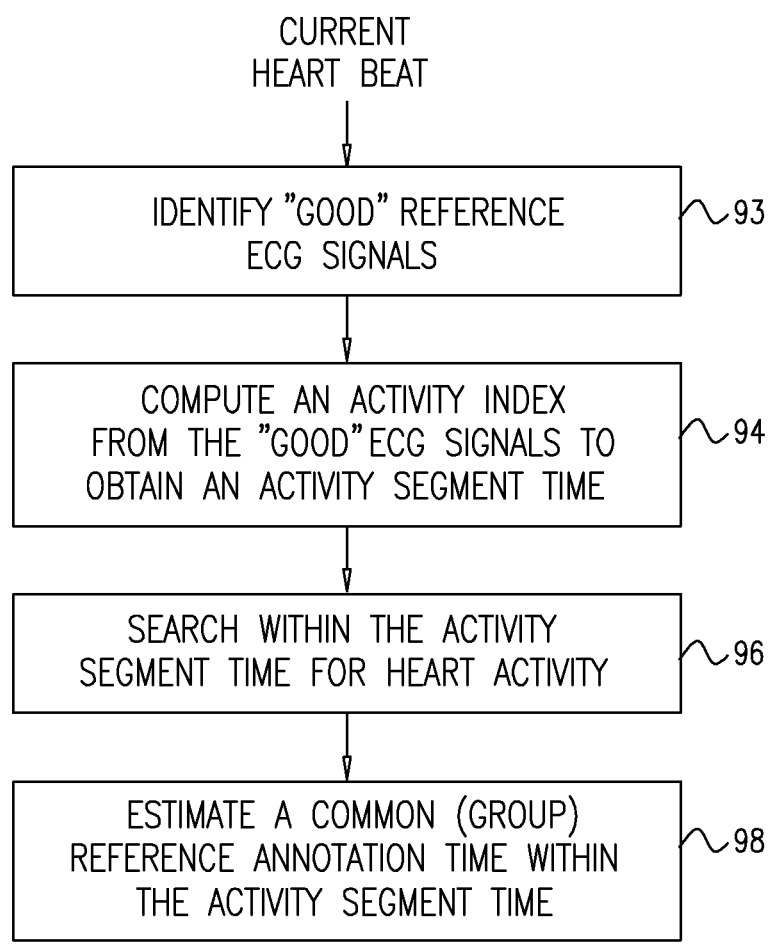
FIG. 4 is a flow chart that schematically illustrates a method for calculating a reference annotation time, in accordance with an embodiment of the present invention.

FIG. 4 is a flow chart that schematically illustrates a method to calculate a reference annotation time, in accordance with an embodiment of the present invention. In an identifying step 93, reference sub-module 37 in processor 40 selects multiple preferable ("good" or robust) ECG signals from among the reference ECG signals for the current heart beat, by applying a signal quality criterion to be described later. In a computing step 94, ECG module 36 computes an activity index from the selected preferable ECG signals (also to described in the embodiments below) to obtain an activity segment time.

In a searching step 96, ECG module 36 searches with the activity segment time for heart activity for the current heart beat. The activity segment time is located in a time interval which is the effective width of the activity index taken at an adaptive threshold level as will be described later. The adaptive threshold level can be estimated as a value dependent upon the noise level of the activity index from activity segment times determined from previous cardiac cycles (heart beats). ECG module 36 evaluates the mapping and/or reference ECG signals for cardiac activity for the current heat beat within the activity time segment. In an estimation step 98, ECG module 36 estimates, or computes, a common (group) reference annotation time within the activity time segment.

The embodiments described in the flowcharts of FIG. 3 and FIG. 4 discuss the computation of the reference annotation time from multiple ECG reference channels used for LAT mapping. It should be noted, but by not by way of limitation of the embodiments described herein, that when user 28 (e.g., doctor 28) assesses the suspected cardiac pathology and decides whether to map the ventricles or atria, different ECG reference signals may be used.

For example, when ventricular mapping is performed, catheter 24B may be placed in the ventricles (as shown in FIG. 2 where catheter 24B is in the right ventricle) to receive the mapping ECG signals in step 80. BS electrodes 29 are used in steps 84 and 86 to compute the reference annotation signal for computing the ventricular LAT map in step 88.

Similarly, when atrial mapping is performed, catheter 24B may be placed in the atria (not shown in FIG. 2) in step 80. However, intra-cardiac catheter 24A in coronary sinus 62 is used to acquire the reference ECG signals from IC electrodes 60A . . . 60E, which are used in steps 84 and 86 to compute the reference annotation signal for computing the atrial LAT map in step 88. The different methods for computing the reference annotation time in step 86 given the cases where BS or IC reference electrodes are chosen are now described below.

Figure 5:
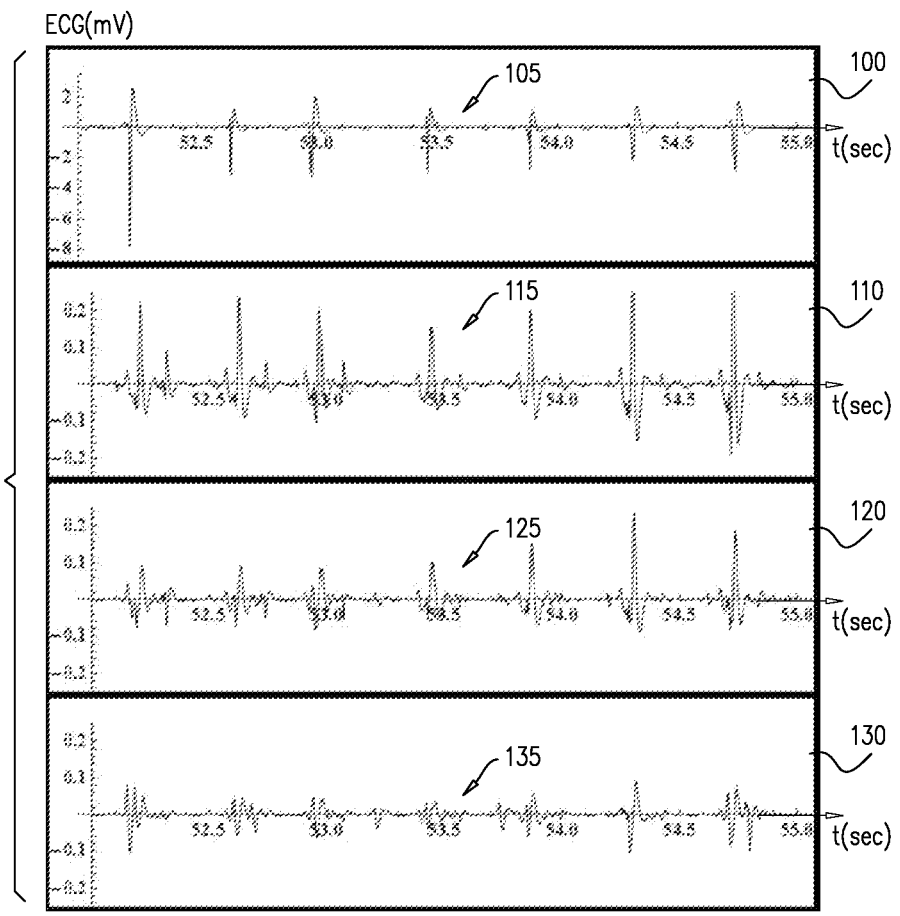
FIG. 5 is a diagram showing multiple ECG signals used in determining a reference annotation time, in accordance with an embodiment of the present invention.

Reference Annotation Time Determined from Body Surface ECG Reference Signals FIG. 5 is a diagram showing reference ECG signals used in determining the reference annotation time, in accordance with an embodiment of the present invention. Traces 100, 110, 120, and 130 show the ECG signals measured from four respective body surface electrodes 29, chosen from among the six electrodes shown in FIG. 1. Traces 100, 110, 120 and 130 are also referred to as ECG channels CH1 . . . CH4, respectively. The ECG signals in FIG. 5 are shown merely for conceptual clarity and not by way of limitation of the embodiments of the present invention.

As described previously, the portion of the ECG signals associated with a particular cardiac cycle, or heart beat, are detected at the same time for BS electrodes, as is the case shown in FIG. 5. This feature can be seen in comparing CH1 ECG Peak 105, CH2 ECG Peak 115, CH3 ECG Peak 125, and CH4 ECG Peak 135, all occurring at about 53.5 sec. It is clear from the morphology of the four peaks shown in FIG. 5 that peaks 105, 115, and 125 have a discernible R-peak and peak 135 does not. The ECG channels detecting peaks 105, 115, and 125 are thus flagged by reference ECG sub-module 37 as preferable, robust or "good" ECG reference channels, and peak 135 (e.g., CH4) is a "bad" channel.

Reference ECG sub-module 37 is configured to distinguish "good" ECG from "bad" ECG channels in step 93 by applying a signal quality criterion to the ECG signals. The signal quality criterion may comprise the signal-to-noise ratio (SNR), uniformity of signals within a predefined time slice by processor 40 of the ECG signal for a given heart beat as shown in FIG. 5, by noise and pulse interference due to any system impairments, or by any other suitable criterion. Module 37 flags the "good" ECG reference channels for further signal processing of the reference annotation time. These criteria can be applied to both IC and BS reference ECG signals.

In some embodiments, processor 40 defines and uses an activity index function (AI) as a metric defined to derive an activity segment time from the robust, or "good" ECG reference channels in step 96. In the description that follows, i denotes the indices of the preferred (robust, "good") channels, and $N_{good}$ is the number of good ECG channels. Essentially, AI comprises an equivalent ECG function that combines the energy information in all of the "good" ECG waveforms into one function from which the activity segment time is computed. The activity segment time basically assists processor 40 in computing the position of the system reference annotation within the segment.

For BS ECG reference electrodes, the activity index $AI^{BS}$ can be computed, for example, as:

$$AI^{BS} = \{\Sigma_{i=1}^{N_{good}} \text{SMOOTH}[\text{ABS}[ECG_i]]\}^2 \quad (1)$$

where $ECG_i$ is the $i^{th}$ "good" ECG waveform, ABS[ ] is the absolute value applied to the ECG waveform, and SMOOTH[ ] is a smoothing function applied to the individual waveform. SMOOTH may comprise, for example, a rectangular window function, a Gaussian window function, a Bartlett window function, or any suitable smoothing function.

Figure 6:
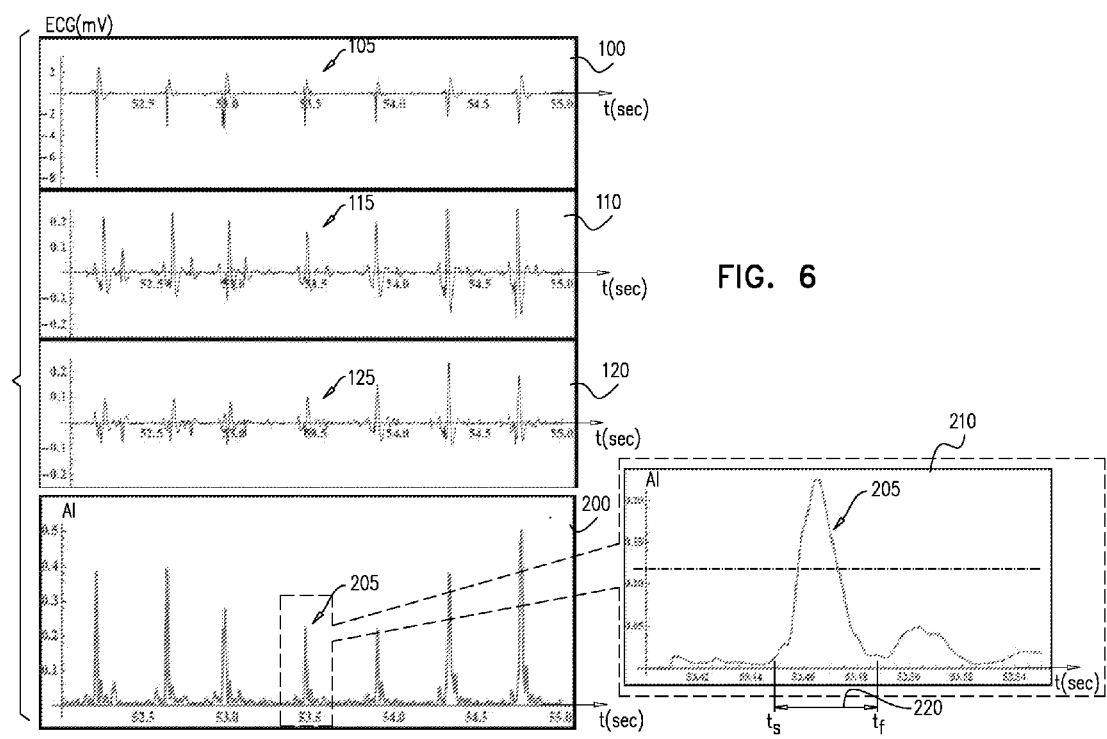
FIG. 6 is a diagram showing a trace of an activity index computed from multiple ECG signals, in accordance with an embodiment of the present invention.

FIG. 6 is a diagram that shows a trace 200 of an activity index computed from ECG signals, in accordance with an embodiment of the present invention. "Good" ECG traces, (e.g., trace 100, trace 110 and trace 120 from FIG. 5) are shown here. Activity index $AI^{BS}$ trace 200 is computed from traces 100, 110 and 120 in step 94 (which have been selected as preferable ECG signals by processor 40). An AI peak 205 corresponding to ECG peaks 105, 115, and 125 can be seen in FIG. 6. An inset 210 shows a blowup of AI peak 205. An activity segment time 220 is shown along the time axis in inset 210 from start time $t_s$ to finish time $t_f$.

The width of pulse activity segment 220 is typically set by setting, or applying, an adaptive threshold (shown as a dashed horizontal line) on pulse waveform 205, for example, according to noise levels outside of the activity segment. The adaptive threshold is determined by monitoring a time interval over a few cardiac cycles to determine the adaptive threshold.

However, endpoints of the segment defining the activity segment are typically wider than the width of the adaptive threshold. For example, the adaptive threshold may be set at a certain margin above the amplitude of the ECG signal outside the activity segment. The activity segment width may be set to lie between the intersections of the ECG signal with the threshold, possibly with a certain margin.

In some embodiments, processor 40 in step 98 may derive the reference annotation time from the maximum ECG peak of the individual "good" ECG channels or any other suitable landmark in the morphology of the ECG signal, since the reference ECG signals acquired from BS electrodes 29 fall within the same time interval.

In other embodiments, the reference annotation time of the group ($RA_{group}$) can be also derived in step 98 by computing the normalized first moment of the activity index function (e.g., equation (1)):

$$RA_{group} = \int_{t_s}^{t_f} t AI^{BS}(t) dt / \int_{t_s}^{t_f} AI^{BS}(t) dt \quad (2)$$

where $t_s$ and $t_f$ are the start and finish extremum, respectively, of time segment 220. Alternatively, processor 40 may derive the reference annotation time from the activity index function in any other suitable way. Once the reference annotation time is derived by the methods taught above, the reference annotation time can be applied to the mapping data to obtain the local activation times (LAT) for the activation map in step 88.

Reference Annotation Time Determined from Intra-Cardiac ECG Reference Signals

Typically, intra-cardiac reference electrodes 60A . . . 60E receive ECG signals with a larger time spread relative to the body-surface electrodes. The larger time spreads are due, for example, to the different arrival times of the ECG signals at the different IC reference electrodes. As a result, processor 40 typically uses a different activity index function to compute the activity segment time from intra-cardiac ECG reference data in step 94.

For IC ECG reference channels, the $N_{good}$ "good" channels are chosen in step 93 by the methods described previously. In some embodiments, the IC activity index $AI^{IC}$ function is given by:

$$AI^{IC} = {}^{N_{good}-1}\sqrt{\frac{\prod_{i=1}^{N_{good}} \text{SMOOTH}[ABS[ECG_i]]}{\sum_{i=1}^{N_{good}} \text{SMOOTH}[ABS[ECG_i]]}} \quad (3)$$

The group activity index in equation (3) is used in step 94 to obtain the activity segment time (analogously to BS segment time 220 in FIG. 6).

Given the time differences for a given heart beat in the received ECG reference signal on each of the multiple reference electrodes, in an embodiment ECG module 36 uses the IC group activity segment in step 96 to identify time intervals where there is cardiac activity in each individual channel. The group, or system, reference annotation time is computed in step 98 from the individual reference annotation times of the individual "good" channels.

Processor 40 may compute the individual reference annotation time $RA_i$ of the $i^{th}$ IC ECG "good" channel (e.g., [ECG (t)]$_i$) from among the $N_{good}$ channels in a number of methods. First, reference sub-module 37 may be configured to identify a signal characteristic on the morphology of the intra-cardiac ECG signal as cited in the reference above. Typical signal characteristics used to define the reference allocation time of [$ECG_i(t)$] may comprise the time at which the peak maximum of the absolute value of ECG signal occurs, the time at which the minimum of the derivative of the ECG signal occurs, the time at which a center of energy of the complete ECG signal occurs, the time at which a first indication of the ECG signal occurs, or any suitable point on the morphology of [$ECG_i(t)$].

In some embodiments, reference sub-module 37 may use a point along the morphology of SMOOTH[ABS[$ECG_i$]] to obtain $RA_i$. In other embodiments, reference sub-module 37 may use the normalized first moment of SMOOTH[ABS[$ECG_i$]] to obtain $RA_i$.

To calculate the group, or system, reference annotation time ($RA_{group}$) in step 98 for ultimately computing the LATs in step 88 from the mapping data (e.g., from mapping electrodes 70), reference sub-module 37 computes an average of individual channel reference time $RA_i$ in some embodiments using:

$$RA_{group} = \frac{1}{N_{good}} \sum_{i=1}^{N_{good}} RA_i \quad (4)$$

In other embodiments, the group reference annotation time ($RA_{group}$) may be computed in step 98 from a weighted average:

$$RA_{group} = \sum_{i=1}^{N_{good}} w_i RA_i \quad (5)$$

where the weight factor $w_i$ is given by:

$$w_i = \frac{MAX[ABS[ECG_i]]}{\sum_{i=1}^{N_{good}} MAX[ABS[ECG_i]]} \quad (6)$$

and MAX[ABS[ ]] operator computes the maximum of absolute signal amplitude of $ECG_i$.

Methods for Handling Impairments in Intra-Cardiac ECG Signals Used for Computing the Reference Annotation Time In the acquisition of the multiple reference ECG waveforms (e.g., $ECG_i$) in step 84 and subsequent computation of the group reference annotation time, $RA_{group}$, in step 86, a number of signal impairments in [$ECG$]$_i$ acquisition may occur. For example, as the heart beats, reference catheter electrodes 60A . . . 60E contacting the moving tissue may lose electrical contact. In one cardiac cycle, a particular ECG channel may be a "good" channel. However in the next cardiac cycle, there may be no ECG signal in the same ECG channel due to loss of electrode tissue contact or by any other impairment mechanism.

Figure 7A:
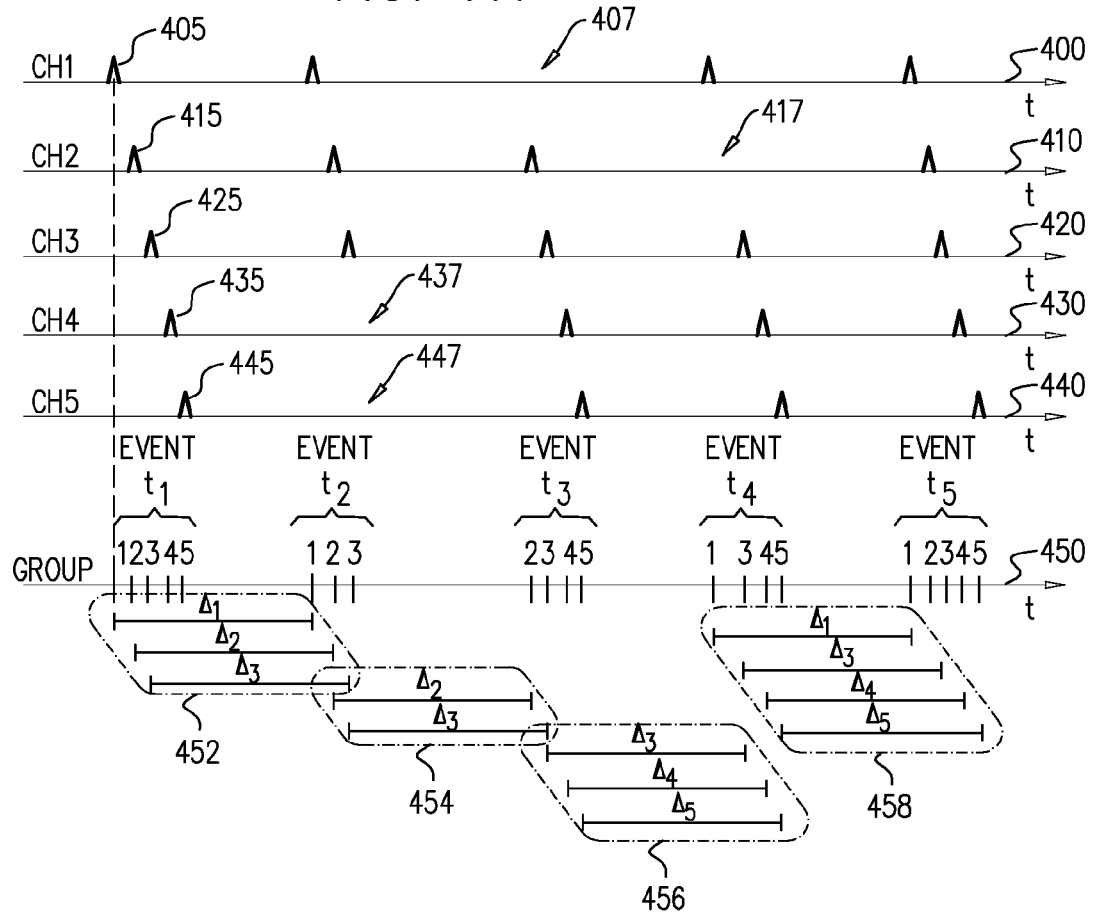
FIG. 7A is a diagram illustrating a method for handling a loss of reference ECG signals, in accordance with an embodiment of the present invention.

FIG. 7A is a diagram illustrating a method for handling a loss of reference ECG signals, in accordance with an embodiment of the present invention. FIG. 7A shows five traces of time-varying ECG signal waveforms: trace 400 from ECG Channel 1 (CH1), trace 410 from ECG Channel 2 (CH2), trace 420 from ECG Channel 3 (CH3), trace 430 from ECG Channel 4 (CH4), and trace 440 from ECG Channel 5 (CH5), corresponding to the signals received from intra-cardiac reference electrode 60A . . . 60E, respectively.

In the exemplary embodiment shown in FIG. 7A, five cardiac cycles, or heart beats, are shown along the time axis denoted EVENT $t_1$ to EVENT $t_5$ (e.g., heart beat 1-5). In the first cardiac cycle, EVENT $t_1$, there is a time offset between the five "good" ECG signals in the five channels due to the different arrival times of the ECG signal to ECG reference electrodes 60A . . . 60E as seen in signal 405, signal 415, signal 425, signal 435, and signal 445, respectively, measured for the same heart beat.

These signals are mapped onto a trace 450 denoted GROUP. The hash marks denoted 1, 2, 3, 4, and 5 correspond to the time position of signals 405, 415, 425, 435, and 445, respectively, in EVENT $t_1$. These hash marks indicate the position of the individual reference annotation times ($RA_i$) for each of the individual channels. The signals and time delays shown in FIG. 7A are merely for conceptual clarity and not by way of limitation of the embodiments of the present invention.

In the next heart beat in EVENT $t_2$, ECG electrode 60D and electrode 60E (corresponding to CH4 and CH5, respectively) have poor contact with the heart tissue. As a result, there is no ECG signal received at a time marker 437 in CH4 and at a time marker 447 in CH5. In EVENT $t_3$, electrode 60A corresponding to CH1 is not in contact with the heart tissue. As a result, there is no ECG signal received at a time marker 407 in CH1.

Similarly, in EVENT $t_4$, electrode 60B corresponding to CH2 is not in contact with the heart tissue. As a result, there is no ECG signal received at a time marker 417 in CH1. Finally, in EVENT $t_5$, all the electrodes contact the heart tissue and reference ECG signal are detected in Channels 1-5.

All of the detected signals from EVENTs $t_1$-$t_5$ on the 5 channels are plotted on GROUP trace 450. As shown in trace 450, reference ECG sub-module 37 received ECG signals from all five channels during EVENTS $t_1$ and $t_5$. However, reference ECG sub-module 37 processes signals from only a part of the five ECG channels during EVENTs $t_2$, $t_3$, and $t_4$. Again, the hash marks denoted 1-5 along trace 450 within the time interval of each cardiac EVENT $t_1$-$t_5$ represents the approximate reference annotation time (e.g., $RA_i$) on the time axes for each channel during the a specific cardiac event, or heart beat.

Calculating the group reference annotation time ($RA_{group}$) during EVENTs $t_2$, $t_3$, and $t_4$ using equations (4) or (5) is problematic, because the missing signals in EVENTs $t_2$, $t_3$, and $t_4$ may cause a skewed group reference annotation time between adjacent cardiac events, even though the signal was present, but not detected.

In some embodiments, reference ECG sub-module 37 is configured to estimate the time interval of the missing ECG signals (e.g., signals 407, 417, 437, and 447) shown in the exemplary example of FIG. 7A. Stated differently, sub-module 37 effectively places a "virtual ECG signal" in place of the missing ECG signal in the proper time interval. $RA_{group}$ is then corrected for the missing ECG signals by the algorithm described below.

First, signals 1-5 are present during EVENT $t_1$, but only signals 1-3 are present during EVENT $t_2$. $\Delta_1$, $\Delta_2$ and $\Delta_3$ are the time intervals between the CH1 ECG signal in EVENT $t_1$ and the CH1 ECG signal in adjacent EVENT $t_2$ shown within a dotted region 452 in FIG. 7A. Similarly, signals 1-3 are present during EVENT t2, but only signals 2-5 are present during EVENT $t_3$. $\Delta_2$ and $\Delta_3$ are the time intervals between the CH1 ECG signal in EVENT $t_2$ and the CH1 ECG signal in adjacent EVENT $t_3$ shown in a dotted region 454 and so forth, for time intervals $\Delta_3$, $\Delta_4$, and $\Delta_5$ from EVENT $t_3$ to EVENT $t_4$ in a dotted region 456, and for time intervals $\Delta_1$, $\Delta_3$, $\Delta_4$, and $\Delta_5$ from EVENT $t_4$ to EVENT $t_5$ in a dotted region 458.

In the embodiment presented herein, the assumption is made that the time intervals $\Delta_1$, $\Delta_2$, $\Delta_3$, $\Delta_4$, and $\Delta_5$ are equal, e.g., $\Delta_1 = \Delta_2 = \Delta_3 = \Delta_4 = \Delta_5$ between adjacent cardiac events, or heart beats. Stated differently, $\Delta_i$ is the same from cardiac event $t_{n-1}$ to $t_n$, where n is the index of the cardiac event. Hence, even if a signal on a particular channel is missing, this assumption can be used to place a virtual ECG signal in place of the missing signal so as to compensate the computed $RA_{group}$ during each event for one or more missing ECG reference signals as described above during adjacent events.

The operator CROSS on events $t_1$ and $t_2$ is defined as the overlapping channel indices of the ECG signal present in two adjacent events. For example, signals 1-5 (e.g., CH1-CH5) are present during EVENT $t_1$, but only signals 1-3 (e.g., CH1-CH3) are present during EVENT $t_2$. Thus, CROSS($t_1$, $t_2$)=1, 2, 3, where Ncross=3 for this case. An average time interval $\Delta^{av}$ based on $\Delta_i$ as defined previously is given by:

$$\Delta^{av} = \frac{1}{N_{cross}} \sum_i^{N_{cross}} \Delta_i \quad (7)$$

wherein summing is performed over the interval defined by the CROSS operator.

In the embodiments of the present invention, the group annotation times computed using Eqns. (4) and (5) by processor 40 are corrected for missing ECG channels from the $t_{n-1}$ event to the $t_n$ event during each cardiac cycle. The corrected group reference annotation time $RA_{group}[t_n]$ is given by:

$$RA_{group}[t_n]=RA_{group}[t_{n-1}]+\Delta_{t_{n-1},t_n}^{AV} \quad (8)$$

where n=2, 3, . . . and $RA_{group}[t_1]$ can be calculated as weighted average of the individual reference channel annotations. The methods taught herein to correct the reference annotation time in step 86 ensures correct LAT computations in computing the activity and propagation maps in step 88.

A second possible impairment arises when reference catheter 24A is placed within coronary sinus 62 as shown in FIG. 2. The narrowness of the coronary sinus is known to hold the reference catheter fixed in one place to help in maintaining good contact of electrodes 60A . . . 60E with the heart tissue. (This reduces the occurrence of the first impairment of missing ECG signals described previously.) However, the coronary sinus is located roughly between the boundary of the atria and the ventricles. As a result, electrical activity of both the atria and the ventricles may be received simultaneously by the electrodes.

Figure 7B:
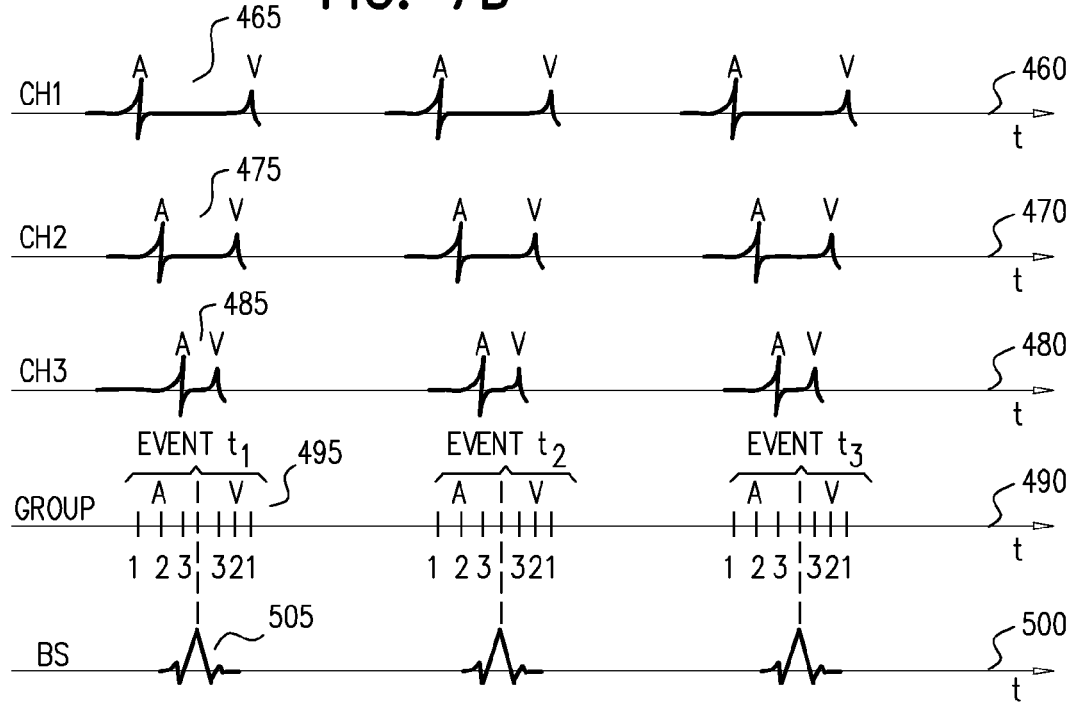
FIG. 7B is an illustration of atrial and ventricular ECG signals sensed by ECG reference electrodes, in accordance with an embodiment of the present invention.

FIG. 7B is an illustration of atrial and ventricular electrocardiogram (ECG) signals received by ECG reference electrodes, in accordance with an embodiment of the present invention. In this exemplary embodiment, three ECG channels denoted CH1-CH3 are considered here, that are signals received by IC reference electrodes 60A, 60B, and 60C on catheter 24A when placed within the coronary sinus. The time-varying ECG waveforms received by IC reference electrodes 60A, 60B, and 60C are shown respectively in traces 460, 470, and 480.

In this case, the received ECG waveforms may comprise signatures of both an atrial (A) ECG component and a ventricular (V) ECG component. However, in using the reference ECG waveforms obtained when catheter 24A is placed in coronary sinus 62 (e.g., typically for atrial mapping as described previously), processor 40 must be able to distinguish both the A and V component, and to eliminate the V component in step 86 not needed for the atrial mapping procedure.

The atrial electrical wave front starts from the SA node, propagates down the atrial tissue, and interacts the ECG reference electrodes. The ventricular wave front starts with the triggering of the AV node after a delay (≈70 ms) relative to the initiation of the atrial wave front. However, the electrical activity spread from the AV node along the center of the heart (above the septum) to the bottom of the heart and wraps around and propagates upward over the ventricles. The ventricular electrical wave front interacts with the IC reference ECG electrodes in another direction that of the atrial electrical wave front.

Thus, if the atrial ECG waveform in CH1 leads CH2, the ventricular ECG waveform in CH1 will lag CH2. Again, these time variations are intrinsically due to the different arrival times of the activity wave fronts to the spatially separated probes as previously described.

These effects can be seen the A and V waveform behavior in comparing signals 465, 475, and 485 in channels CH1, CH2, and CH3, respectively, for EVENT $t_1$. The hash marks denoted 1, 2, and 3 at marker 495 correspond to the time position of signals 465, 475, and 485, respectively, in EVENT $t_1$. The A and V components are delineated clearly showing the effect of oppositely propagating A and V wave fronts in the ECG waveform behavior as described previously. These hash marks roughly represent the A and V reference annotation time for each of the individual channels.

The A and V signatures are distinguished by two methods in step 86. In some embodiments, reference ECG sub-module 37 distinguishes between the A and V signatures by analyzing the morphology of the A and V component waveforms.

In other embodiments, reference ECG sub-module 37 identifies the A and V components by comparing the body surface (BS) ECG waveform (trace 490) to the IC waveforms (traces 460, 470, and 480) in the same cardiac event. The BS waveform always occurs after the A component and before the V component. This behavior is seen in assessing the position of signal 505 to signals 465, 475, and 485. The A and V ECG signals shown in FIG. 7B are merely for conceptual clarity and not by way of limitation of the embodiments of the present invention.

Reference ECG sub-module 37 distinguishes the A and V signatures and computes the appropriate reference annotation time in step 86 using all of the methods described previously. Map ECG sub-module 41 then applies the reference annotation time to the ECG mapping data to create the LAT map in step 88.

Although the embodiments described herein mainly address the mapping of cardiac activity, the methods and systems described herein can also be used in other applications, where electro-physiological activity also exists such as in gastroenterology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
receiving a plurality of mapping electro-cardiogram (ECG) signals from respective mapping electrodes coupled to a surface of a heart of a patient;
receiving multiple reference ECG signals from respective reference electrodes coupled to the patient;
jointly processing the multiple reference ECG signals by selecting from among the reference ECG signals two or more preferable ECG signals that meet a signal quality criterion, and deriving the single timing reference from the selected preferable ECG signals, so as to produce a single timing reference indicative of cardiac cycle timing of the heart; and
applying the single timing reference to the mapping ECG signals.

2. Apparatus, comprising:
an interface, which is configured to receive a plurality of mapping electro-cardiogram (ECG) signals from respective mapping electrodes coupled to a surface of a heart of a patient, and to receive multiple reference ECG signals from respective reference electrodes coupled to the patient; and
a processor, which is configured to jointly process the multiple reference ECG signals by selecting from among the reference ECG signals two or more preferable ECG signals that meet a signal quality criterion, and deriving the single timing reference from the selected preferable ECG signals, so as to produce a single timing reference indicative of cardiac cycle timing of the heart, and to apply the single timing reference to the mapping ECG signals.

3. A method, comprising:
receiving a plurality of mapping electro-cardiogram (ECG) signals from respective mapping electrodes coupled to a surface of a heart of a patient;
receiving multiple reference ECG signals from respective reference electrodes coupled to the patient;
jointly processing the multiple reference ECG signals by combining two or more of the reference ECG signals to produce an equivalent ECG function, and deriving the single timing reference from the equivalent ECG function, so as to produce a single timing reference indicative of cardiac cycle timing of the heart; and
applying the single timing reference to the mapping ECG signals.

4. The method according to claim 3, wherein deriving the single timing reference comprises applying an adaptive threshold to the equivalent ECG function.

5. The method according to claim 3, wherein deriving the single timing reference comprises computing a first moment of the equivalent ECG function.

6. A method, comprising:
receiving a plurality of mapping electro-cardiogram (ECG) signals from respective mapping electrodes coupled to a surface of a heart of a patient;
receiving multiple reference ECG signals from respective reference electrodes coupled to the patient;
jointly processing the multiple reference ECG signals by computing two or more timing references for two or more of the reference ECG signals, respectively, and deriving the single timing reference from the two or more timing references, so as to produce a single timing reference indicative of cardiac cycle timing of the heart; and
applying the single timing reference to the mapping ECG signals.

7. The method according to claim 6, wherein deriving the single timing reference comprises averaging the two or more timing references.

8. The method according to claim 7, wherein averaging the two or more timing references comprises calculating a weighted average of the two or more timing references depending on respective maximum amplitudes of the respective reference ECG signals.

9. A method, comprising:
receiving a plurality of mapping electro-cardiogram (ECG) signals from respective mapping electrodes coupled to a surface of a heart of a patient;
receiving multiple reference ECG signals from respective reference electrodes coupled to the patient;
jointly processing the multiple reference ECG signals by detecting a missing peak in one of the reference ECG signals, and compensating for the missing peak in computation of the single timing reference, so as to produce a single timing reference indicative of cardiac cycle timing of the heart; and
applying the single timing reference to the mapping ECG signals.

10. A method, comprising:
receiving a plurality of mapping electro-cardiogram (ECG) signals from respective mapping electrodes coupled to a surface of a heart of a patient;
receiving multiple reference ECG signals from respective reference electrodes coupled to the patient;
jointly processing the multiple reference ECG signals by distinguishing between atrial and ventricular ECG signatures in the reference ECG signals, so as to produce a single timing reference indicative of cardiac cycle timing of the heart; and
applying the single timing reference to the mapping ECG signals.

11. Apparatus, comprising:
an interface, which is configured to receive a plurality of mapping electro-cardiogram (ECG) signals from respective mapping electrodes coupled to a surface of a heart of a patient, and to receive multiple reference ECG signals from respective reference electrodes coupled to the patient; and
a processor, which is configured to jointly process the reference ECG signals by combining two or more of the reference ECG signals to produce an equivalent ECG function, and deriving the single timing reference from the equivalent ECG function, so as to produce a single timing reference indicative of cardiac cycle timing of the heart, and to apply the single timing reference to the mapping ECG signals.

12. The apparatus according to claim 11, wherein the processor is configured to derive the single timing reference by applying an adaptive threshold to the equivalent ECG function.

13. The apparatus according to claim 11, wherein the processor is configured to derive the single timing reference by computing a first moment of the equivalent ECG function.

14. Apparatus, comprising:
an interface, which is configured to receive a plurality of mapping electro-cardiogram (ECG) signals from respective mapping electrodes coupled to a surface of a heart of a patient, and to receive multiple reference ECG signals from respective reference electrodes coupled to the patient; and
a processor, which is configured to jointly process the reference ECG signals by computing two or more timing references for two or more of the reference ECG signals, respectively, and deriving the single timing reference from the two or more timing references, so as to produce a single timing reference indicative of cardiac cycle timing of the heart, and to apply the single timing reference to the mapping ECG signals.

15. The apparatus according to claim 14, wherein the processor is configured to derive the single timing reference by averaging the two or more timing references.

16. The apparatus according to claim 15, the processor is configured to average the two or more timing references by calculating a weighted average of the two or more timing references depending on respective maximum amplitudes of the respective reference ECG signals.

17. Apparatus, comprising:
- an interface, which is configured to receive a plurality of mapping electro-cardiogram (ECG) signals from respective mapping electrodes coupled to a surface of a heart of a patient, and to receive multiple reference ECG signals from respective reference electrodes coupled to the patient; and
- a processor, which is configured to jointly process the reference ECG signals by detecting a missing peak in one of the reference ECG signals, and compensating for the missing peak in computation of the single timing reference, so as to produce a single timing reference indicative of cardiac cycle timing of the heart, and to apply the single timing reference to the mapping ECG signals.

18. Apparatus, comprising:
- an interface, which is configured to receive a plurality of mapping electro-cardiogram (ECG) signals from respective mapping electrodes coupled to a surface of a heart of a patient, and to receive multiple reference ECG signals from respective reference electrodes coupled to the patient; and
- a processor, which is configured to jointly process the reference ECG signals by distinguishing between atrial and ventricular ECG signatures in the reference ECG signals, so as to produce a single timing reference indicative of cardiac cycle timing of the heart, and to apply the single timing reference to the mapping ECG signals.

\* \* \* \* \*